(12) United States Patent
Dougherty et al.

(10) Patent No.: US 8,755,555 B2
(45) Date of Patent: Jun. 17, 2014

(54) ADJUSTABLE AND CONVERTIBLE AUDIO HEADPHONES

(75) Inventors: Christopher Dougherty, Doylestown, PA (US); Steven D. Roberts, Larchmont, NY (US)

(73) Assignee: The Echo Design Group, Inc., New York, NY (US)

( * ) Notice: Subject to any disclaimer, the term of this patent is extended or adjusted under 35 U.S.C. 154(b) by 15 days.

(21) Appl. No.: 13/446,321

(22) Filed: Apr. 13, 2012

(65) Prior Publication Data

US 2013/0272560 A1 Oct. 17, 2013

(51) Int. Cl.
*H04R 25/00* (2006.01)

(52) U.S. Cl.
USPC ............ 381/378; 381/370; 381/374; 381/379

(58) Field of Classification Search
USPC .......................... 381/370–371, 374, 377–383
See application file for complete search history.

(56) References Cited

U.S. PATENT DOCUMENTS

| | | | |
|---|---|---|---|
| 2,420,245 A | 5/1947 | Hurst | |
| 2,615,169 A | 10/1952 | Maxant | |
| 3,119,119 A | 1/1964 | Millinger et al. | |
| 5,293,647 A | 3/1994 | Mirmilshteyn et al. | |
| 5,345,512 A * | 9/1994 | Lee | 381/377 |
| 5,406,037 A * | 4/1995 | Nageno et al. | 381/377 |
| 5,862,241 A | 1/1999 | Nelson | |
| D430,140 S | 8/2000 | Roman | |
| D473,539 S | 4/2003 | O'Leary | |
| 6,654,966 B2 | 12/2003 | Rolla | |
| 6,724,906 B2 * | 4/2004 | Naksen et al. | 381/379 |
| D512,708 S | 12/2005 | Harris, Jr. et al. | |
| D538,261 S | 3/2007 | Taylor et al. | |
| D573,581 S | 7/2008 | Gondo et al. | |
| D600,674 S | 9/2009 | Brennwald | |
| D673,520 S | 1/2013 | Tan | |

\* cited by examiner

*Primary Examiner* — Suhan Ni

(74) *Attorney, Agent, or Firm* — Wiggin and Dana LLP; Gregory S. Rosenblatt

(57) ABSTRACT

A set of adjustable and convertible headphones includes a headband, an adjustment member, and an earpiece. The adjustment member is connected to the headband by a hinge; earpiece has a channel receiving the adjustment member and is slidably connected to the adjustment member. Rotation of the adjustment member with respect to the headband is spring-loaded in only one direction. The adjustment member and the earpiece in combination include a detent mechanism for resisting sliding movement of the earpiece with respect to the adjustment member. The adjustment member may be completely removed from the channel, thereby disconnecting the earpiece from the headband. The earpiece may then be replaced by another ear covering (e.g., an earmuff, an ear protector, etc.) as desired. The replacement ear covering may include an audio speaker, for example an audio/earmuff combination earpiece.

5 Claims, 19 Drawing Sheets

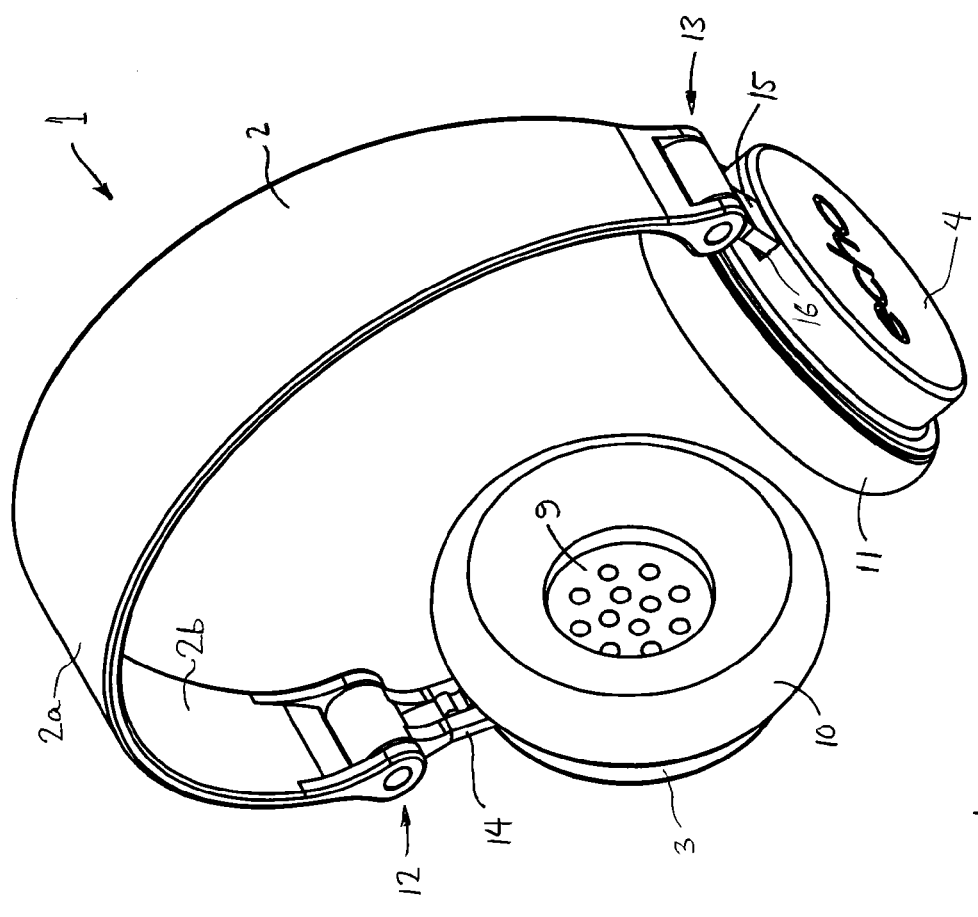

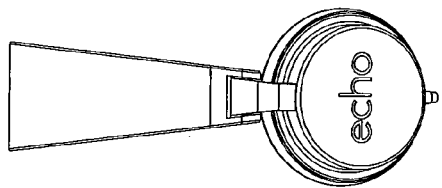
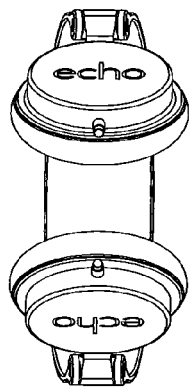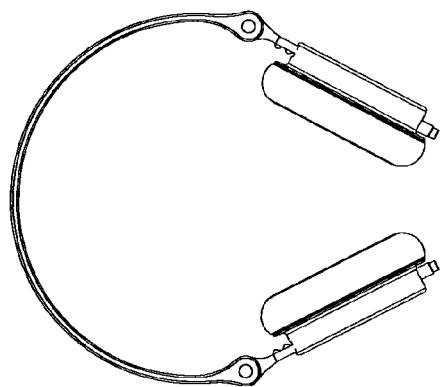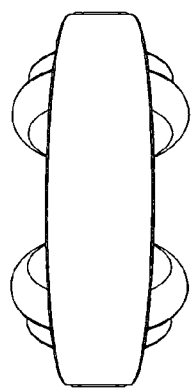
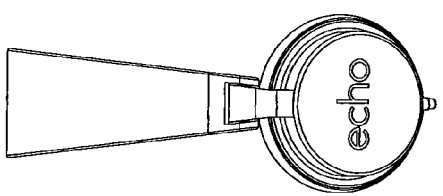
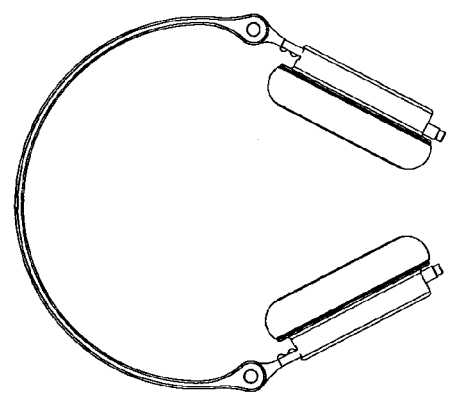

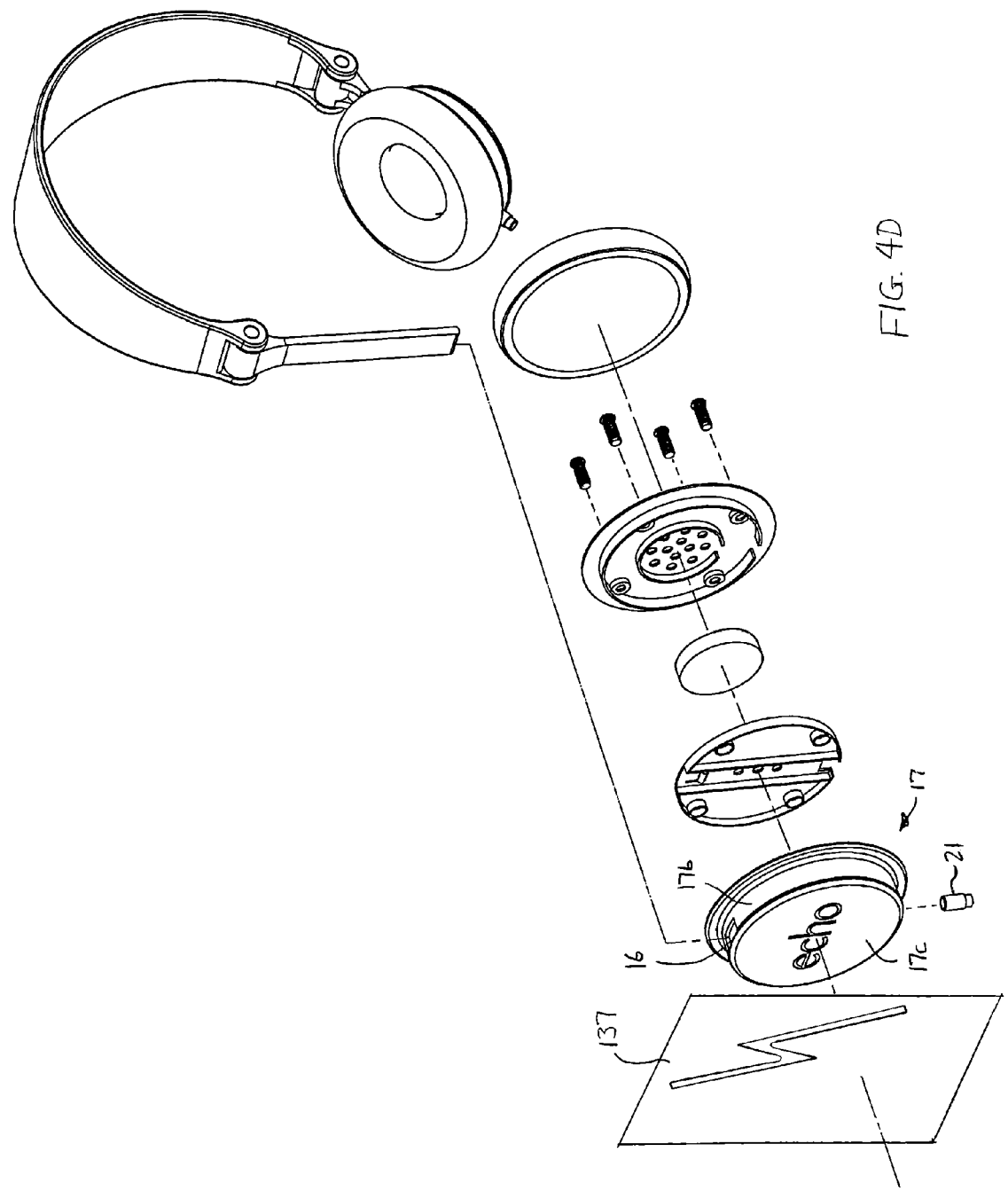

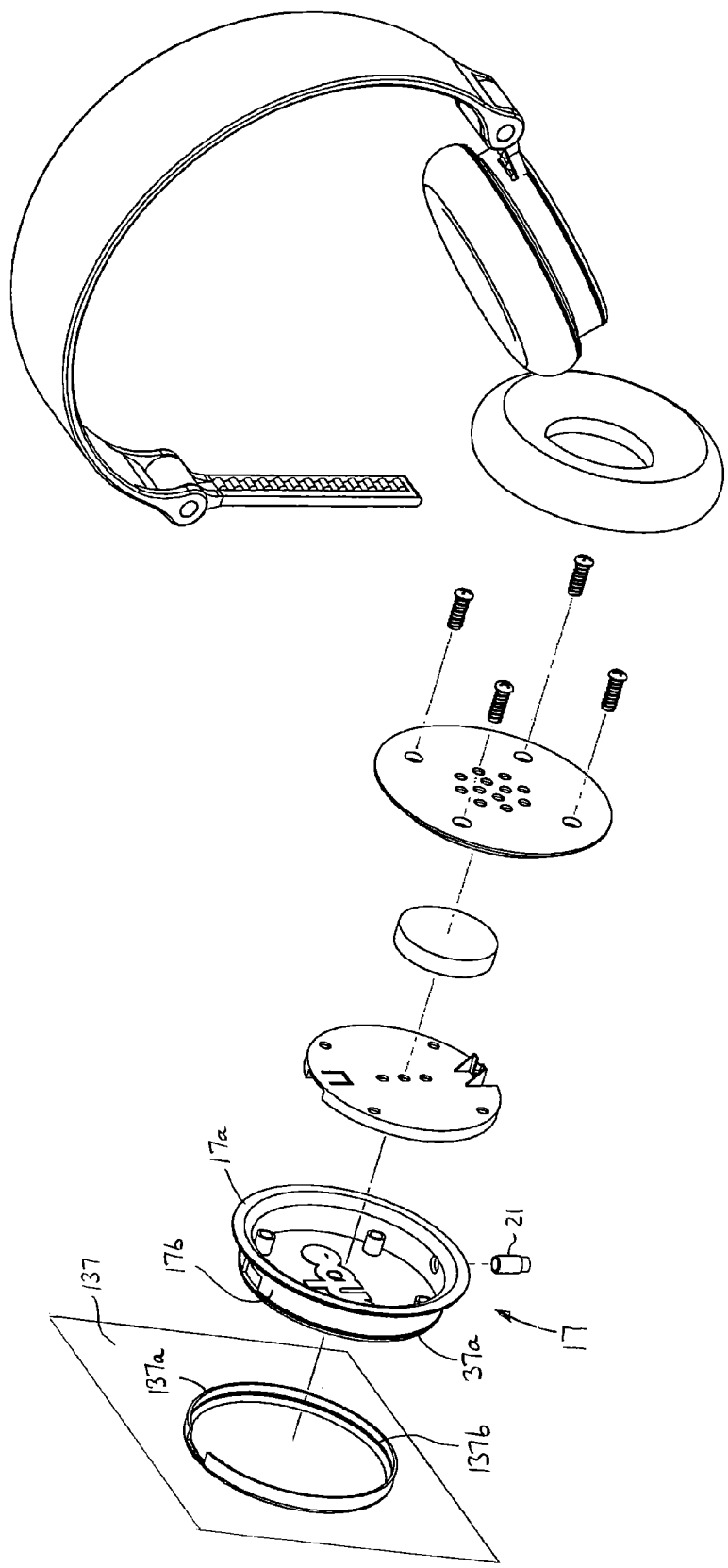

ADJUSTABLE AND CONVERTIBLE AUDIO HEADPHONES

CROSS-REFERENCE TO RELATED APPLICATIONS

The present application is related to a co-pending U.S. design patent application U.S. Ser. No. 29/418,231 that is now U.S. Pat. No. D683,327, titled "ADJUSTABLE AND CONVERTIBLE AUDIO HEADPHONES", having a common inventor and filed on even date.

FIELD OF THE DISCLOSURE

This disclosure relates to personal audio equipment, and more particularly to adjustable headphones.

BACKGROUND OF THE DISCLOSURE

Audio headphones are in common use, and accordingly it is desirable to provide headphones that fit comfortably on the user's head while isolating the user's ears from ambient noise. If the headphones have a band fitting over the top of the user's head, this should adjust for comfort; the earpieces should be separately adjustable so that they fit snugly against the user's ears. Generally, simpler and less expensive designs are less adjustable and therefore less comfortable.

In cold weather, a headphone user may need to exchange the headphone for earmuffs, in effect exchanging audio enjoyment for thermal comfort. It is desirable to provide headphones which offer a wide range of adjustment for comfort and that may also serve as earmuffs or other types of ear protectors, and at the same time serve as audio headphones.

SUMMARY OF THE DISCLOSURE

According to an aspect of the disclosure, adjustable and convertible headphones are provided including a headband, an adjustment member, and an earpiece. The adjustment member is connected to the headband at an end thereof by a hinge. The earpiece has a channel formed therein for receiving the adjustment member; the earpiece is thus slidably connected to the adjustment member. The hinge includes a spring mechanism so that rotation of the adjustment member with respect to the headband via the hinge is spring-loaded in a first direction and not spring-loaded in an opposite second direction. The adjustment member and the earpiece in combination include a detent mechanism for resisting sliding movement of the earpiece with respect to the adjustment member. The headband may be formed of a flexible plastic.

In an embodiment, the hinge has a pin through coaxial holes in the headband and the adjustment member; the adjustment member has a hollow formed in the interior thereof surrounding the pin; and a spring is disposed in the hollow. The adjustment member has a tab radially intruding into the hollow, so that rotation of the adjustment member with respect to the headband in the first direction causes the tab to contact and compress the spring, and rotation of the adjustment member with respect to the headband in the second direction does not cause the tab to contact the spring.

In another embodiment, the detent mechanism includes a flexible tab, connected to the earpiece, having a protrusion seated in a notch in the adjustment member. Flexing the tab to unseat the protrusion from a first notch, in response to force applied in a direction along the channel, permits the adjustment member to slide in the channel. The protrusion then seats in a second notch, unless the adjustment member is completely removed from the channel, thereby disconnecting the earpiece from the headband. The earpiece may then be replaced by another ear covering (e.g., an earmuff, an ear protector, etc.) as desired. In a particular embodiment, the earpiece includes an audio speaker, and the earpiece is also configured as an earmuff with an outer covering over the audio speaker, so that the headphones are convertible to audio/earmuff combination headphones.

In another embodiment, the earpiece also includes a removable and interchangeable outer end cap, so that the appearance of the earpiece may be easily changed.

According to another aspect of the disclosure, a method to convert a set of headphones is provided; the headphones include a headband, an adjustment member connected to the headband, and an earpiece slidably connected to the adjustment member. The headphones are converted by sliding the earpiece with respect to the adjustment member in a direction away from the headband to remove the earpiece, and then sliding a replacement earpiece with respect to the adjustment member in a direction toward the headband to connect the replacement earpiece; each of these sliding steps includes applying force to overcome resistance from a detent mechanism. In an embodiment, at least one of the earpiece and the replacement earpiece includes an audio speaker. The replacement earpiece may be an earmuff; in particular, the replacement earpiece may include an audio speaker and be configured as an earmuff with an outer covering over the audio speaker.

According to an additional aspect of the disclosure, a method to adjust a set of headphones is provided; the headphones include a headband having an upper surface and an opposing lower surface, an adjustment member connected to the headband at an end thereof by a hinge including a spring, and an earpiece connected to the adjustment member. The headphones are adjusted by rotating the earpiece in combination with the adjustment member with respect to the headband about the hinge, in an inward direction toward the lower surface of the headband and/or in an opposite outward direction. Rotating the adjustment member in the outward direction past a neutral position causes compression of the spring resulting in resistance to that rotation, and rotating the adjustment member in the inward direction does not cause compression of the spring. The neutral position may be characterized by a portion of the adjustment member contacting a portion of the spring without compressing the spring.

The foregoing has outlined, rather broadly, the preferred features of the present disclosure so that those skilled in the art may better understand the detailed description of the disclosure that follows. Additional features of the disclosure will be described hereinafter that form the subject of the claims of the disclosure. Those skilled in the art should appreciate that they can readily use the disclosed conception and specific embodiment as a basis for designing or modifying other structures for carrying out the same purposes of the present disclosure and that such other structures do not depart from the spirit and scope of the disclosure in its broadest form.

BRIEF DESCRIPTION OF THE DRAWINGS

FIG. 1 is a perspective view of audio headphones in accordance with an embodiment of the disclosure.

FIGS. 2A-2F are respectively front, left, rear, right, top and bottom views of the headphones of FIG. 1.

FIG. 4D is a partially exploded perspective view of the headphones of FIG. 4B, showing a modified interchangeable outer end cap according to another embodiment of the disclosure.

FIG. 4E is a partially exploded view of the headphones of FIG. 4D, from a different perspective, showing additional details of the modified interchangeable outer end cap.

DETAILED DESCRIPTION

Headphones: headband, earpieces and audio connections

Figure 3:
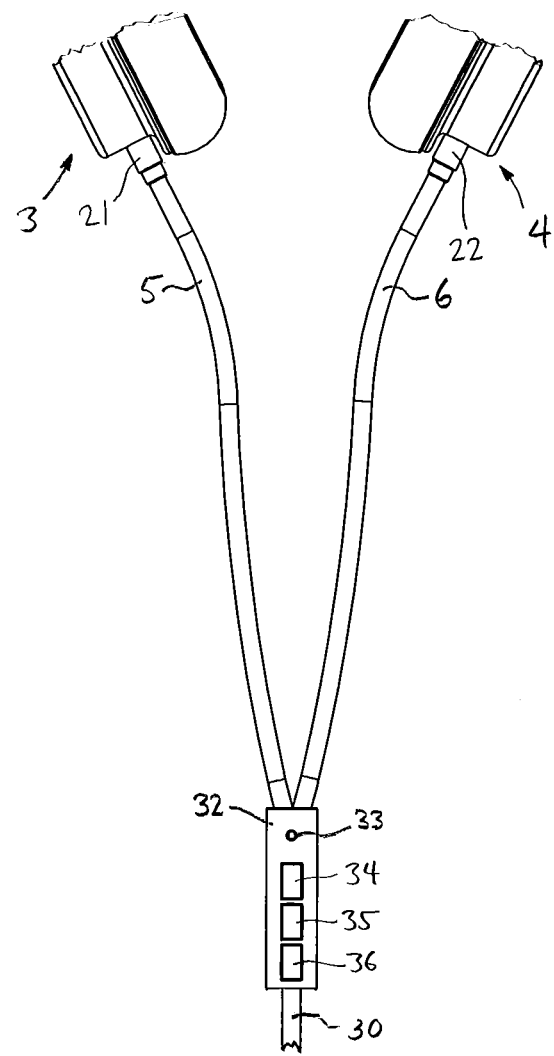
FIG. 3 shows audio signal wires connected to the left and right earpieces and an audio microphone/control unit.

FIG. 1 shows a general perspective view of a set of headphones 1 according to an embodiment of the disclosure. Headband 2 has hinges 12, 13 at the respective ends thereof; the main portion of the headband, between hinges 12 and 13, has an upper surface 2a and an opposing lower surface 2b. Headband 2 is formed from a durable material such as plastic, and is flexible and resilient so that the audio earpieces 3, 4 may be pulled apart from each other when the headphones are put on the user's head, and then fit snugly against the user's ears. The earpieces are connected to a suitable source of audio signal by connectors and wires (not shown in FIG. 1). An audio speaker (one speaker cover 9 visible in FIG. 1) is centrally located on the inside-facing surface of each earpiece. Each earpiece is provided with padding 10, 11 surrounding the speaker and in contact with the ears when the headphones are in use.

In addition to the headband 2 being flexible to accommodate the size of the user's head, each earpiece is adjustable with respect to the headband. At each end of the headband, adjustment members 14, 15 are connected to the headband via hinges 12, 13 respectively. Each adjustment member is received in the corresponding earpiece through opening 16 (one visible in FIG. 1). Each adjustment member independently rotates on its hinge while the distance between the opening and the hinge may be lengthened and shortened, as described more fully below.

FIGS. 2A-2F are respectively front, left, rear, right, top and bottom views of headphones 1.

FIG. 3 shows the audio earpieces of headphones 1 with wires for making connection to the audio source. Wires 5 and 6, connected to earpieces 3 and 4 respectively by connectors 21 and 22, are joined at audio control unit 32 which connects to cable 30. Cable 30 carries both left- and right-channel audio signals and connects to an audio source (not shown). In this embodiment, the audio control unit includes a microphone 33 and track control buttons 34, 35, 36 for "previous song," "pause" and "next song" respectively.

Figure 4A:
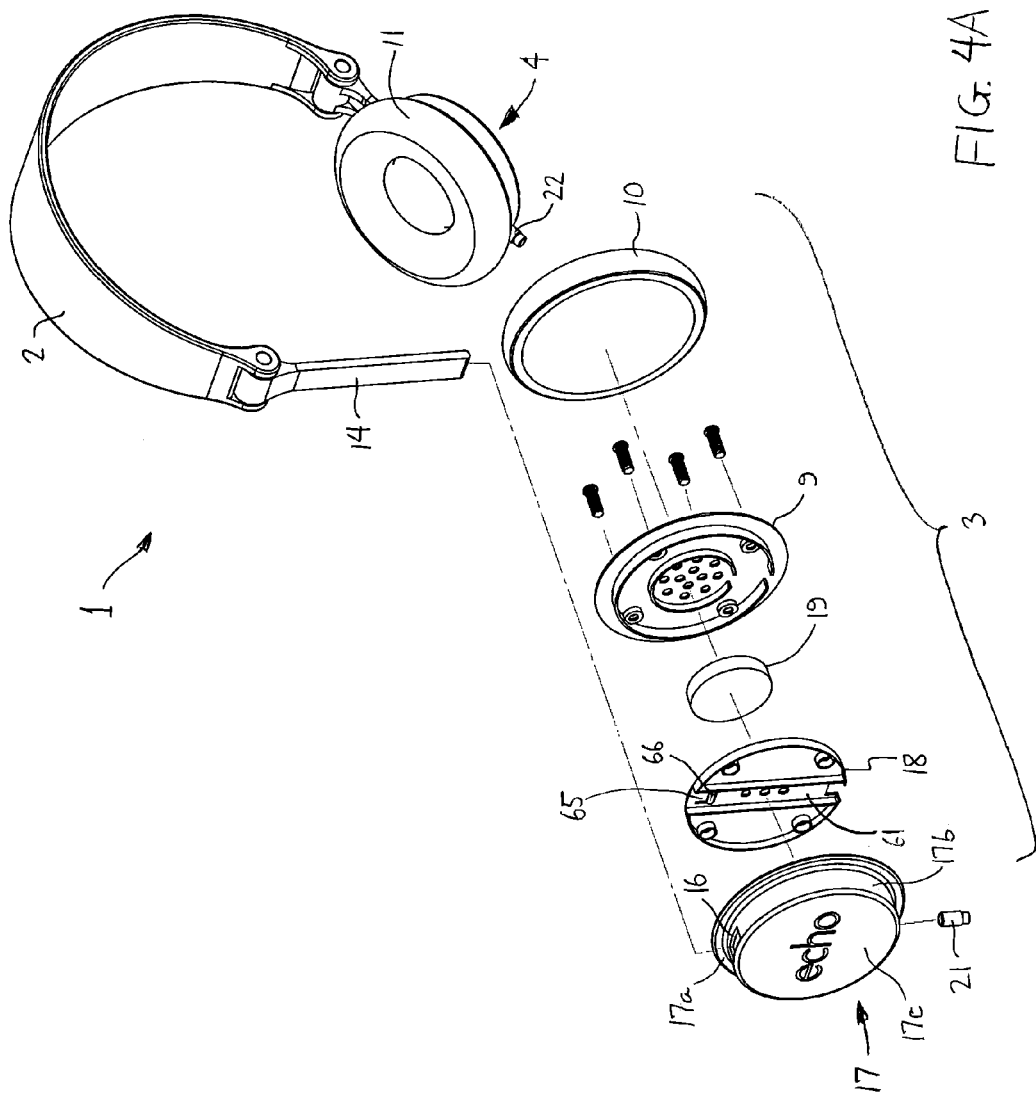
FIG. 4A is a partially exploded perspective view of the headphones of FIG. 1, showing details of an audio earpiece according to an embodiment of the disclosure.

FIG. 4A is a partially exploded view of the headphones of FIG. 1, showing details of audio earpiece 3. Speaker 19 fits into a recess at the back side of speaker cover 9. Speaker cover 9 and channel plate 18 are secured to each other and to end cap 17. Padding 10 fits over the front side of speaker cover 9. Channel plate 18 fits into end cap 17 so that channel 61, formed at the back side of channel plate 18, is aligned with opening 16.

Adjustment member 14 is received in opening 16 and slides in channel 61. A tab structure 65, formed in a wall of channel 61 and having a protrusion 66 extending into the channel, forms a detent mechanism with notches in adjustment member 14 (not shown in FIG. 4). The detent mechanism resists sliding motion of the adjustment member in the channel. Details of a detent mechanism, according to an embodiment, are described below with reference to FIGS. 9-11.

End cap 17 has an inner portion 17a with a diameter greater than that of channel plate 18, a middle portion 17b with a curved surface, and an outer end portion 17c. Middle portion 17b may be cylindrical or tapered; in this embodiment, the inner edge thereof has a greater circumference that the outer edge, so that middle portion 17b is slightly tapered in the outward direction.

Figure 4B:
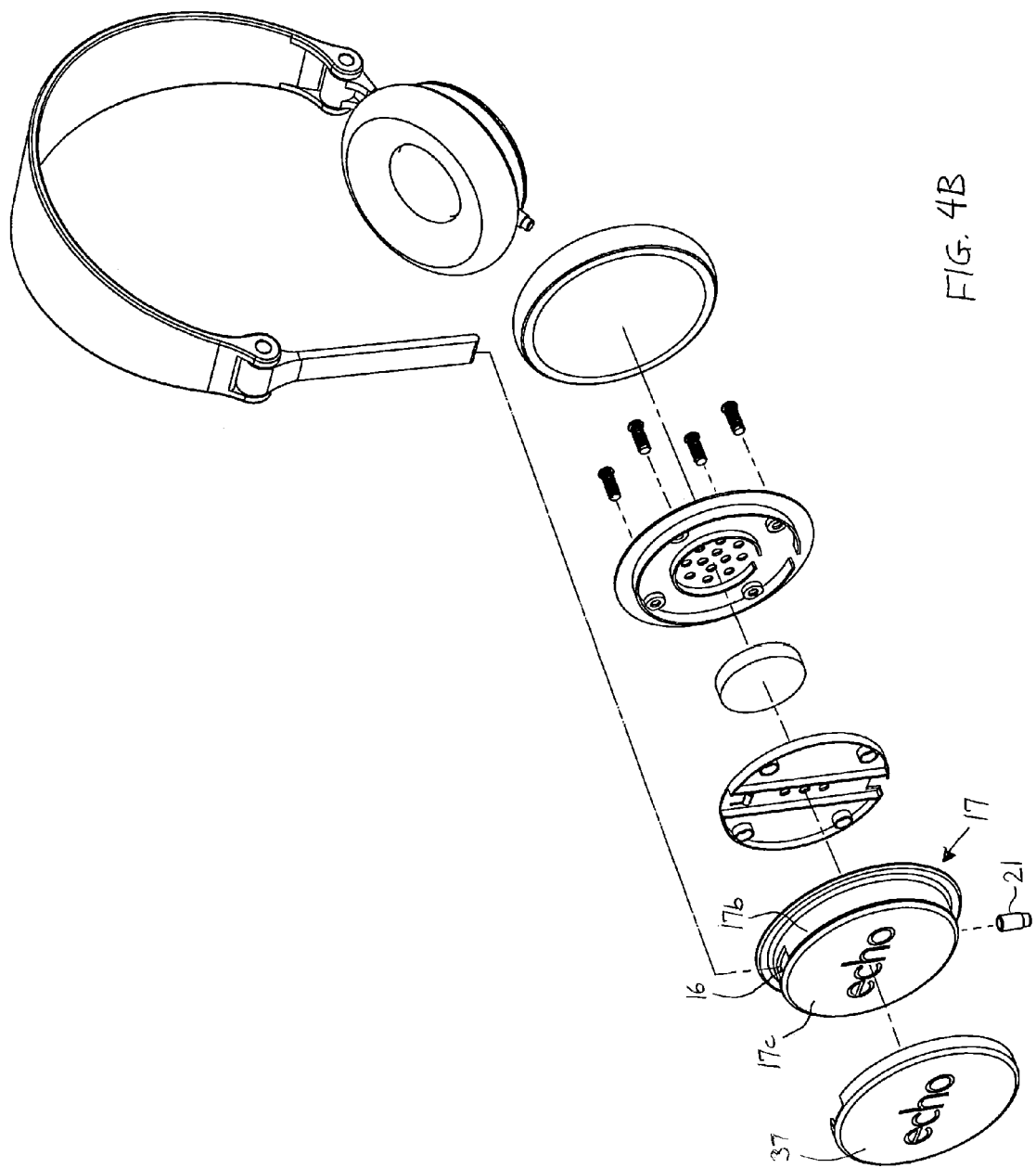
FIG. 4B is a partially exploded perspective view of the headphones of FIG. 4A, showing the addition of an interchangeable outer end cap according to another embodiment of the disclosure.
Figure 4C:
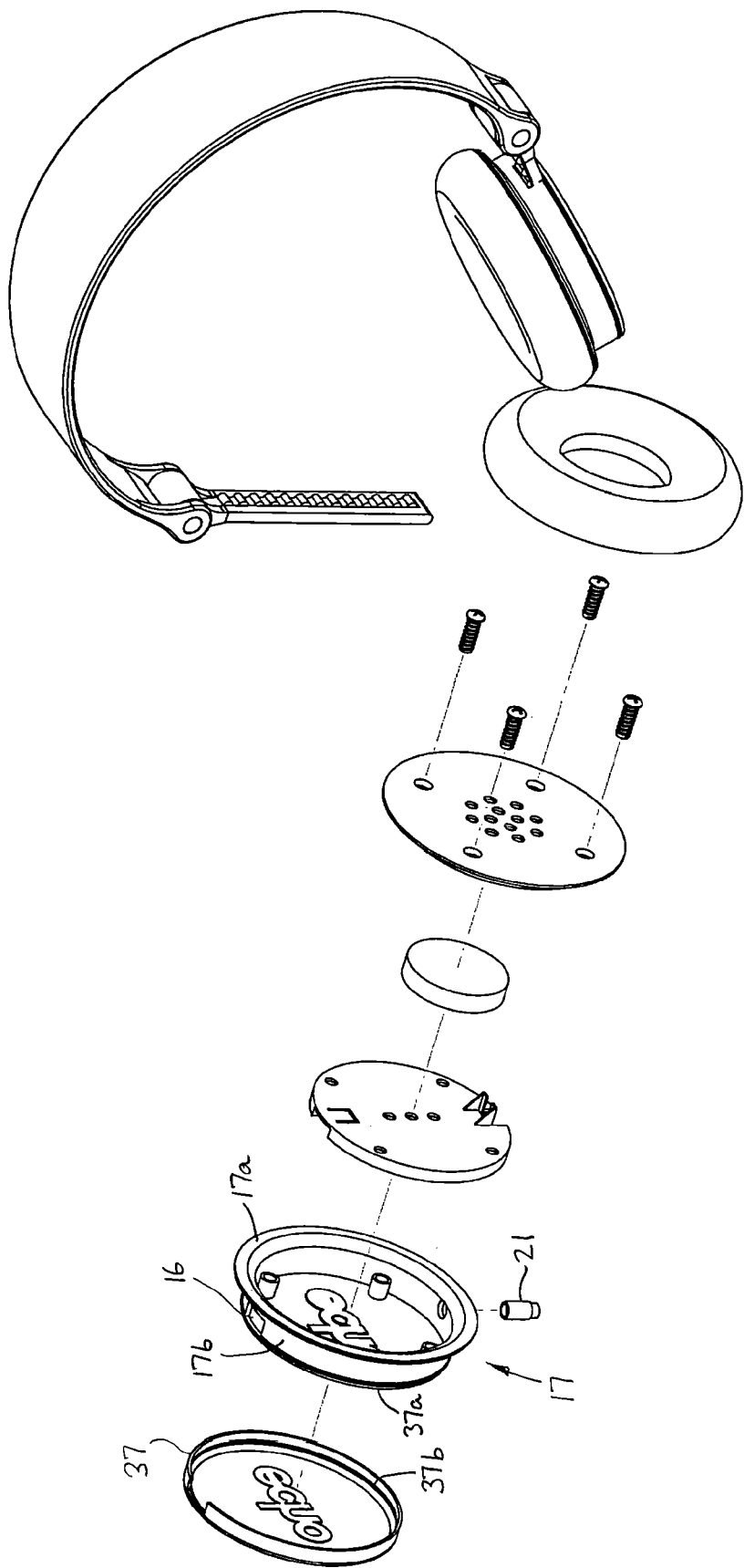
FIG. 4C is a partially exploded view of the headphones of FIG. 4B from a different perspective, showing additional details of the interchangeable outer end cap.

In an embodiment, outer end portion 17c is covered by a removable and interchangeable outer end cap 37, as shown in FIG. 4B. Outer end cap 37 is removably joined to end cap 17 by a slip-fit connection, a snap-fit connection, or the like. As shown in FIG. 4B, outer end cap 37 covers portion 17c and fits around part of portion 17b; the outer end cap 37 is provided with cutouts as required to avoid interfering with opening 16 or connector 21. FIG. 4C is a different perspective view of the embodiment shown in FIG. 4B. In this embodiment, middle portion 17b has a groove 37a formed therein and outer end cap 37 has a bead 37b around a corresponding interior surface, thereby providing a removable snap-fit connection for outer end cap 37 onto end cap 17.

Outer end caps of various designs, sizes, colors, patterns, etc. may thus be interchanged as desired, providing headphones 1 with a varied appearance. For example, outer end cap 37 of FIGS. 4B and 4C may be removed and replaced with a larger outer end cap 137 having a different shape and decoration, as shown in FIGS. 4D and 4E respectively. As best shown in FIG. 4E, a wide variety of outer end caps may be used and interchanged, provided that they fit onto end cap 17. In the example of FIG. 4E, outer end cap 137 has a ring 137a on the inner face thereof, with a bead 137b similar to outer end cap 37 shown in FIG. 4C. Outer end cap 137 thus makes a removable snap-fit connection with groove 37a in middle portion 17b of cap 17.

Headphone adjustment: rotation

Figure 5:
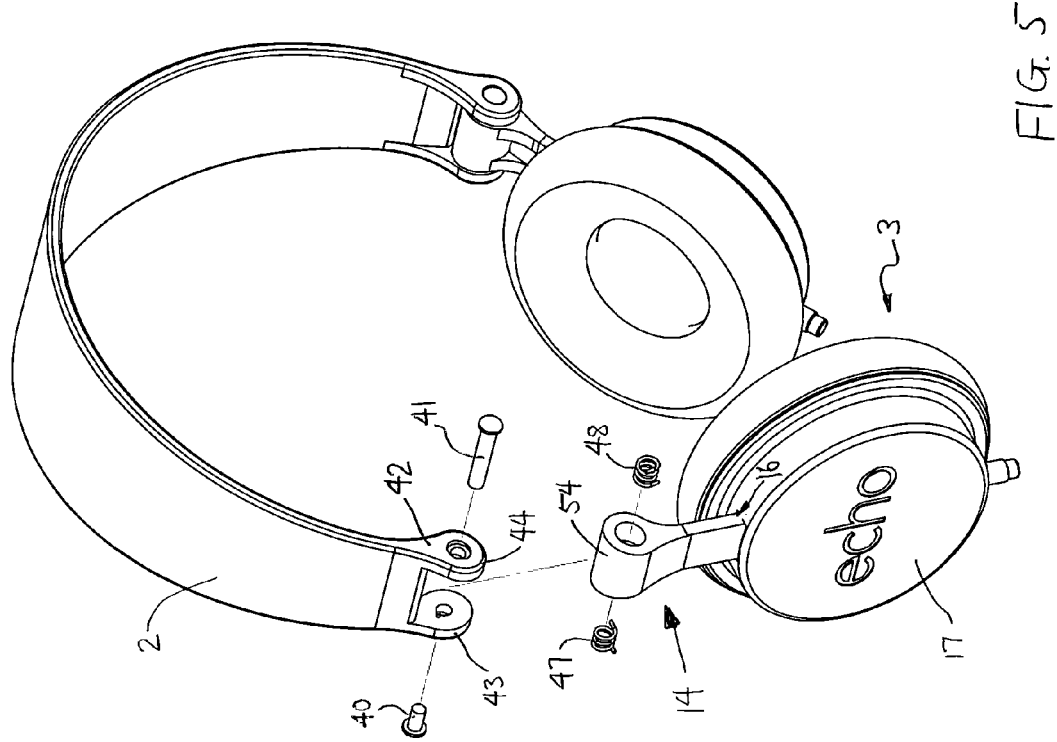
FIG. 5 is another partially exploded view of the headphones of FIG. 1, showing details of a spring-loaded hinge for adjusting an earpiece according to an embodiment of the disclosure.

FIG. 5 is another partially exploded view of the headphones of FIG. 1, showing details of a spring-loaded hinge for adjusting earpiece 3 according to an embodiment of the disclosure. Adjustment member 14 extends from opening 16 toward headband 2 and has a rounded upper end 54. The corresponding lower end of the headband has two arms 43, 44, with space between them to receive rounded end 54. Arms 43, 44 and rounded end 54 all have holes formed therein. Rounded end 54 is placed between arms 43 and 44 so that the holes are aligned to receive hinge pin 41. Fitting 40 secures pin 41 so that the head of pin 41 is held in a recess in arm 44, flush with the adjacent surface 42 of the headband.

The hole in rounded end 54 of adjustment member 14 accommodates springs 47, 48 therein. As shown in FIG. 5, the springs are coils, and surround pin 41. The interior of the hole in rounded end 54 is shaped so that the springs are compressed when adjustment member 14 (with earpiece 3 attached) is rotated outwards (for example, when the user removes the headphones) but are not compressed when adjustment member 14 is rotated inwards (for example, when folding the headphones for storage). Details of the hinge are described below, with reference to FIGS. 6-8.

Figure 6:
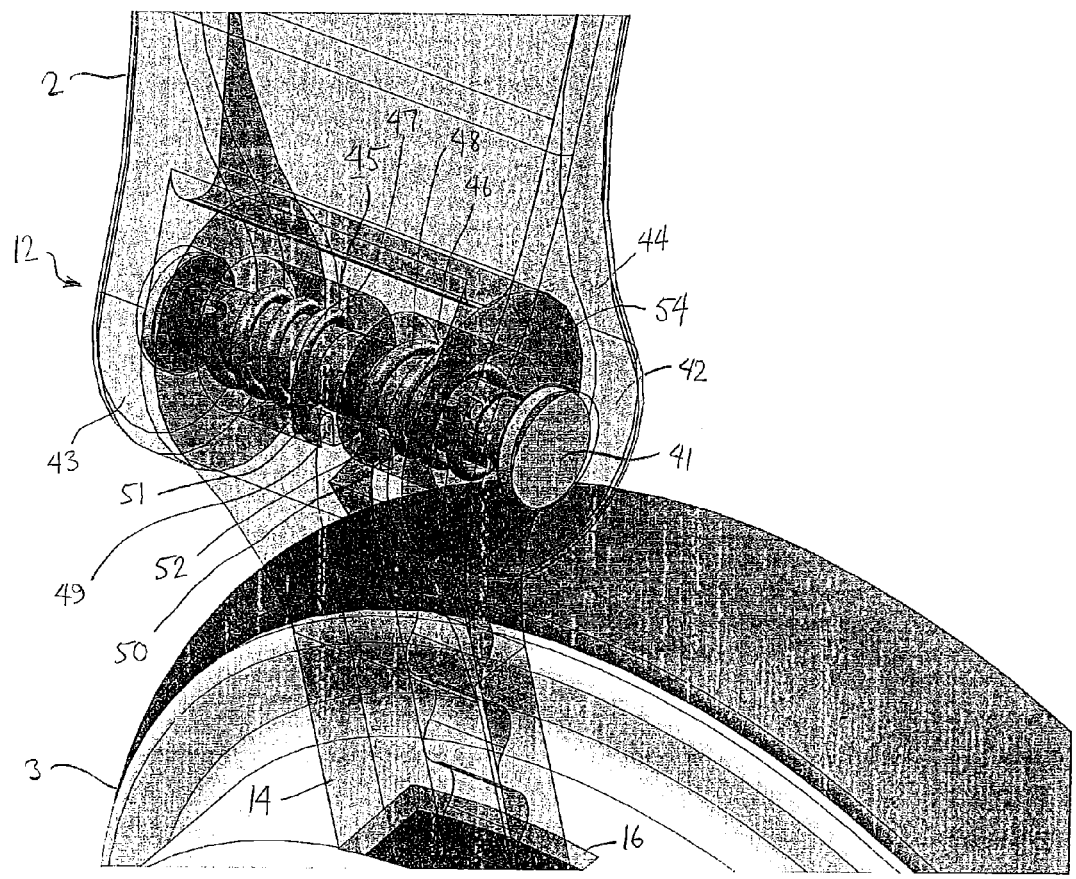
FIG. 6 shows additional details of a spring-loaded hinge used to adjust an earpiece, according to an embodiment of the disclosure.
Figure 7:
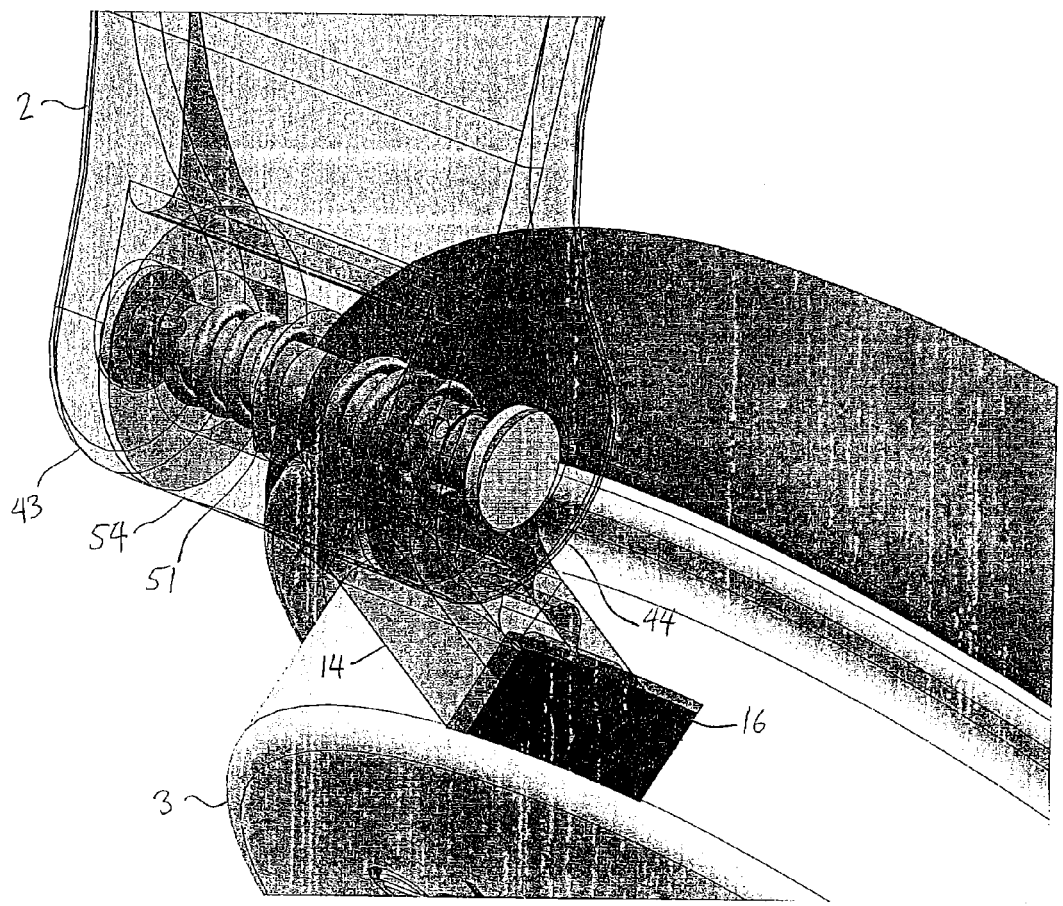
FIG. 7 shows the hinge of FIG. 6 when the earpiece is in a partially folded position (that is, where the earpieces have a distance between them less than in FIG. 6).
Figure 8:
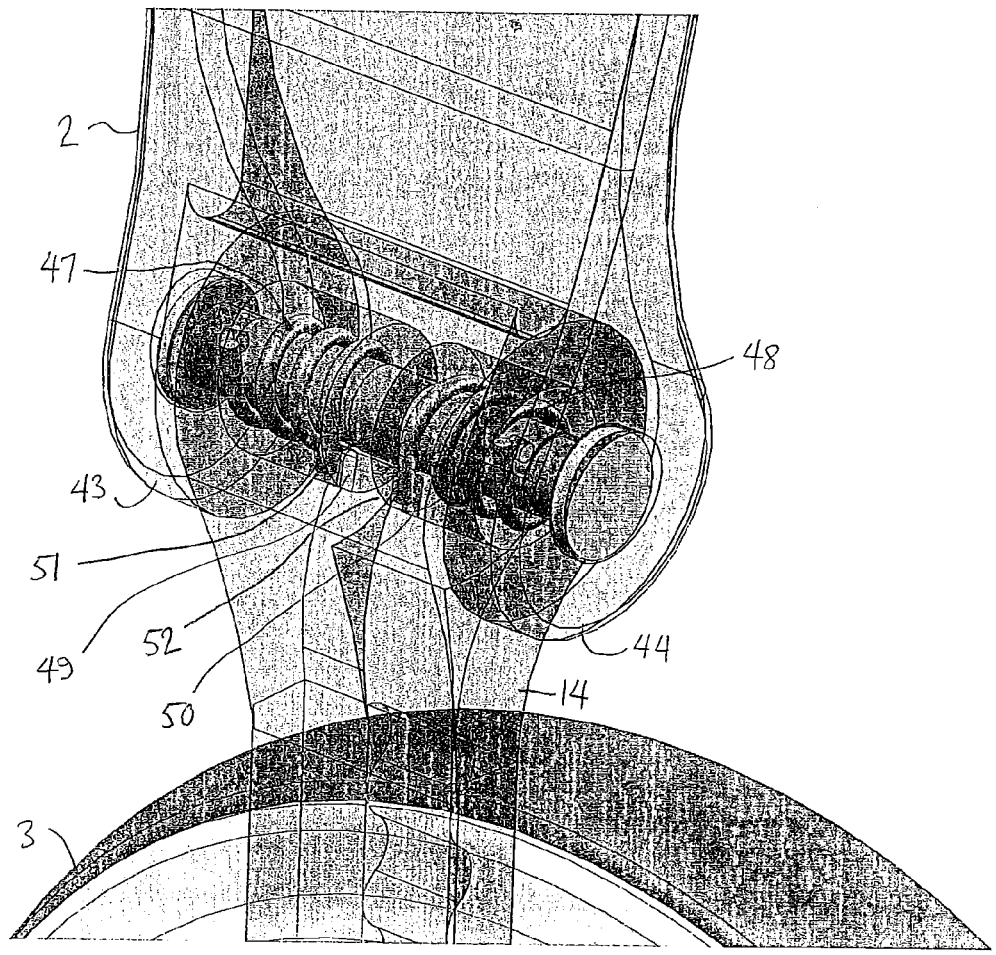
FIG. 8 shows the hinge of FIG. 6 when the earpiece is in an expanded position (that is, where the earpieces have a distance between each other greater than in FIG. 6).

FIGS. 6-8 illustrate rotation of the adjustment members and earpieces with respect to the headband using the hinges, in accordance with an embodiment of the disclosure. Details of hinge 12, which connects headband 2 with adjustment member 14 for adjusting earpiece 3, are illustrated for clarity; it is understood that hinge 13 has a corresponding structure.

Movement of adjustment member 14 relative to headband 2 about hinge 12 is spring-loaded in the outward direction (away from the user's ear) and not spring-loaded in the inward direction (as when folding the earpieces when not in use). FIG. 6 shows the hinge in a neutral position, where the spring is in contact with the adjustment member but is not compressed. The lower end of headband 2 has a fork shape with opposite arms 43, 44 and a space therebetween for receiving the rounded end 54 of adjustment member 14. As shown in FIG. 6, arms 43 and 44 have a rounded profile with a central hole; the rounded end 54 of adjustment member likewise has a central hole. Pin 41 fits through the holes, thereby capturing end 54 between arms 43 and 44. In this embodiment, the opposite ends of pin 41 fit into recesses in arms 43 and 44, so that each end of pin 41 is flush with the adjacent surface 42 of headband 2.

The interior of rounded end 54 has cylindrical hollows 45, 46 coaxial with pin 41, to accommodate springs 47, 48 respectively. Springs 47, 48 are coiled around pin 41. A tab 49 extends from the wall of hollow 45 radially inward into hollow 45; similarly, tab 50 intrudes into hollow 46. An end portion 51 of spring 47 extends tangentially away from pin 41 and radially overlaps tab 49; similarly, an end portion 52 of spring 48 extends tangentially away from pin 41 and radially overlaps tab 50. As shown in FIG. 6, spring end portions 51, 52 are respectively in contact with tabs 49, 50 of the adjustment member 14, but the spring is in a relaxed state.

FIG. 7 shows earpiece 3 and adjustment member 14 rotated inwards with respect to headband 2. Tabs 49, 50 are accordingly rotated away from spring end portions 51, 52. Movement of the earpiece in this direction thus does not encounter any resistance from the springs.

FIG. 8 shows earpiece 3 and adjustment member 14 rotated outwards with respect to headband 2 (and the user's ear). When the adjustment member is rotated in this direction, tabs 49, 50 press against spring end portions 51, 52 respectively, so that springs 47, 48 are compressed. Accordingly, the hinge 12 is spring-loaded to resist rotation in the outward direction.

Headphone adjustment: extension

Figure 9:
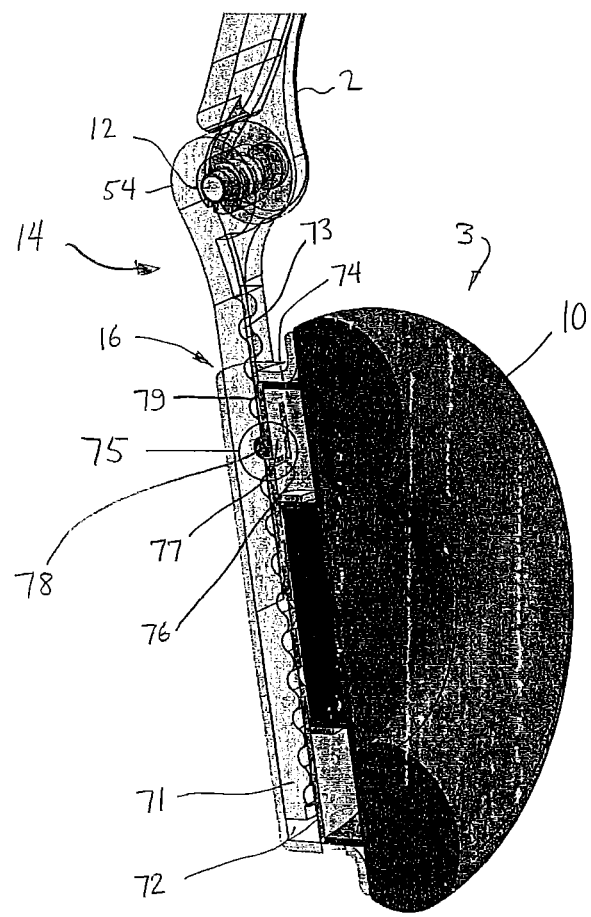
FIG. 9 is a cross-sectional view of an earpiece and an adjusting mechanism for the earpiece, according to an embodiment of the disclosure.
Figure 10:
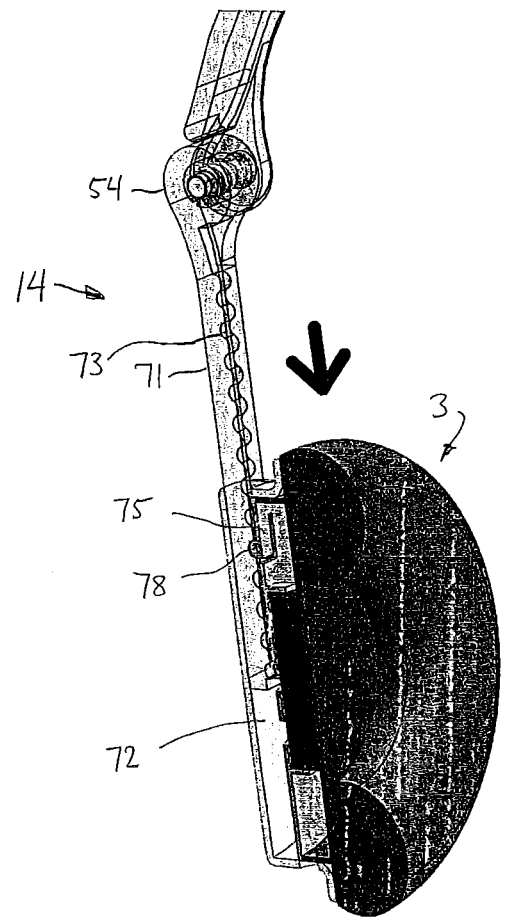
FIG. 10 is a cross-sectional view of an earpiece and an adjustment mechanism, showing the earpiece moved further away from the hinge than in FIG. 9.
Figure 11:
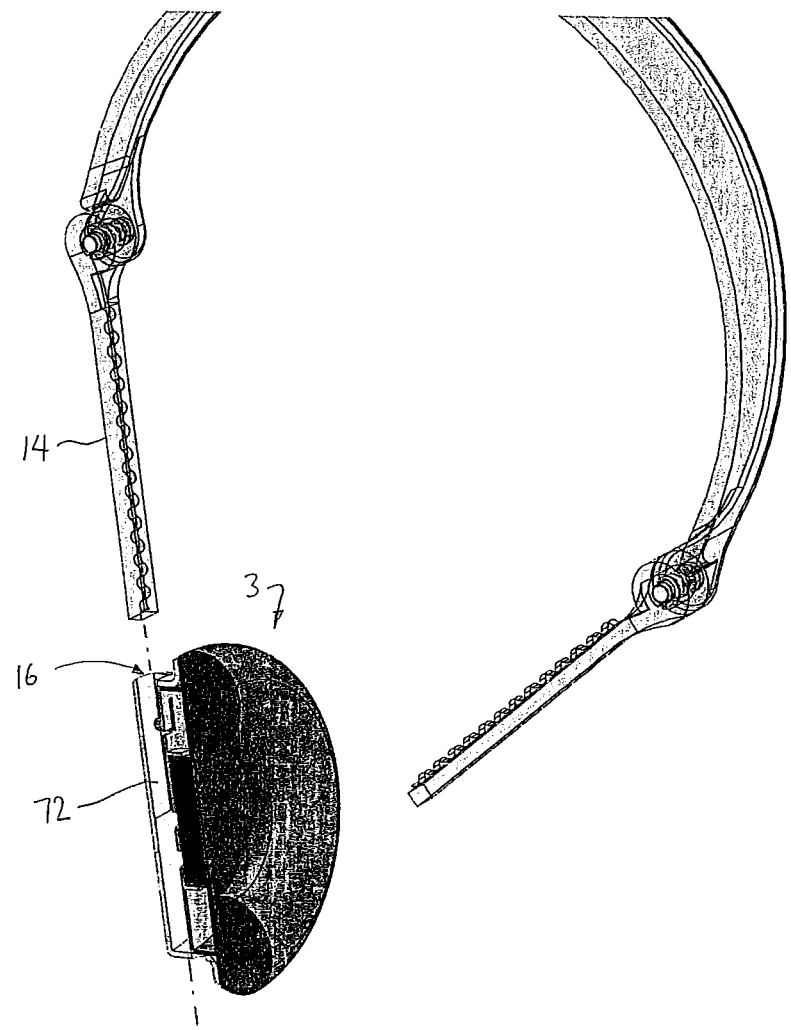
FIG. 11 is a cross-sectional view showing an earpiece moved away from the hinge so that it is removed from the main portion of the headphones.

FIGS. 9-11 illustrate movement of an earpiece relative to its corresponding adjustment member, in order to shorten or lengthen the distance between the earpiece and the headband. Details of earpiece 3 and adjustment member 14, which connects headband 2 with earpiece 3, are illustrated for clarity; it is understood that earpiece 4 and its corresponding adjustment member have a corresponding structure.

FIG. 9 is a cutaway view showing the interior of earpiece 3 and its adjustable connection to headband 2. Adjustment member 14 has a rounded end portion 54 (connected to headband 2 at hinge 12, as described above), and an elongated main portion 71. Earpiece 3 has an interior channel 72, with opening 16 at its upper end. (In this embodiment, channel 72 is closed at its lower end, thus limiting adjustment of the earpiece toward the headband.) Main portion 71 of adjustment member 14 is received in opening 16 and slides inside channel 72, but does not slide freely. The side of the adjustment member closest to the padding 10 of the earpiece (that is, closest to the user's ear) has notches 73 formed therein; the notches have a rounded profile. The wall 74 of the channel opposite the notches has a tab structure 75. A U-shaped slot 76 in wall 74 (L-shaped in the cutaway view of FIG. 9) partially separates a tab portion 77 of the wall from the rest of the wall (the main portion of the wall). Tab portion 77 remains connected to the main portion of the wall at the open end 79 of the U shape. In this embodiment, the channel wall is formed from a resilient plastic; tab portion 77 thus may bend and rotate slightly with respect to wall 74. Tab 75 also has a rounded protrusion 78 extending from tab portion 77 toward the notches 73 in adjustment member 14; protrusion 78 is sized to fit each one of the notches. Tab structure 75 and notches 73 form a detent mechanism that resists movement of adjustment member 14 in channel 72, thereby holding the earpiece in place.

When force is applied in a direction along the channel to move the earpiece relative to the headband, protrusion 78 is pushed out of the notch in which it was seated; tab 75 bends away from the adjustment member, permitting the adjustment member to slide in the channel. Tab 75 bends back to its normal position as the adjustment member moves, with protrusion 78 moving into successive notches 73. When force is no longer applied, tab 75 returns to its normal position, with protrusion 78 seated in a different notch than before. FIG. 10 illustrates the earpiece being forced downward (in the direction of the arrow), causing adjustment member 14 to slide partially out of channel 72 through opening 16 and thus lengthen the distance between the earpiece and the headband. If the earpiece is forced further downward, adjustment member 14 may slide completely out of channel 72, so that the earpiece is detached from the headband (see FIG. 11).

Convertible headphones: earmuffs and audio/earmuff combination

Figures 12A, 12B:
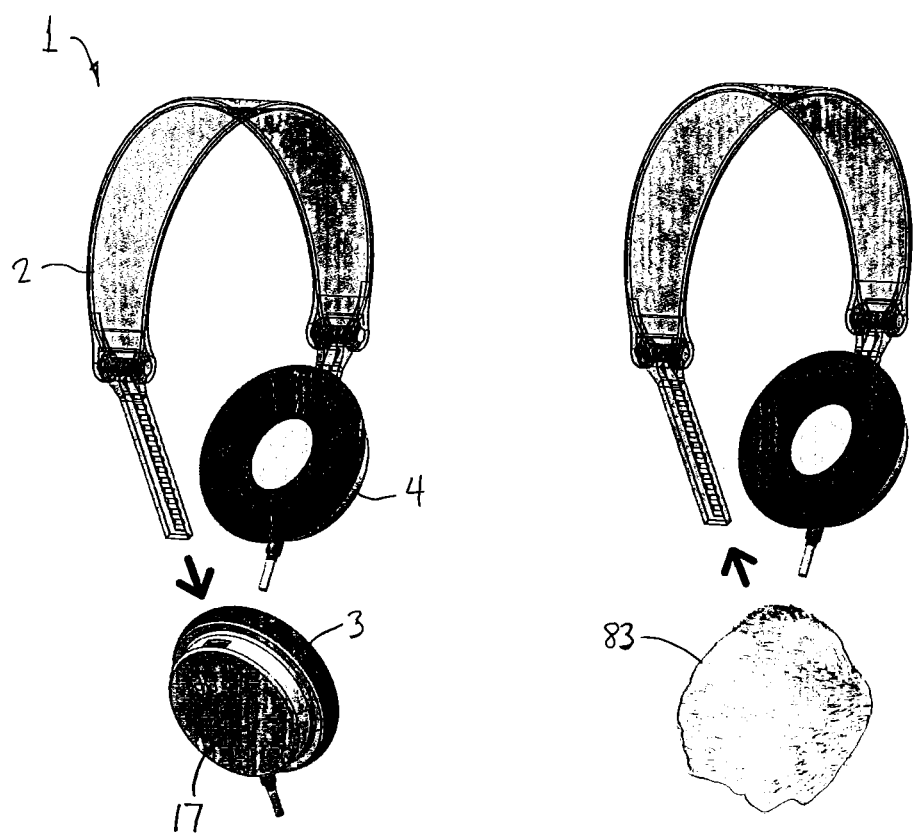
FIG. 12A is a perspective view showing an earpiece removed from the main portion of the headphones.
FIG. 12B is a perspective view showing replacement of the earpiece removed in FIG. 10A with an earmuff, according to an embodiment of the disclosure.

FIGS. 12A and 12B illustrate converting headphones 1 into earmuffs, according to an embodiment of the disclosure. In FIG. 12A, earpiece 3 is forced in the direction of the arrow to detach it from the headband. Earmuff 83 is then attached to the headband, as shown in FIG. 12B.

Figure 13:
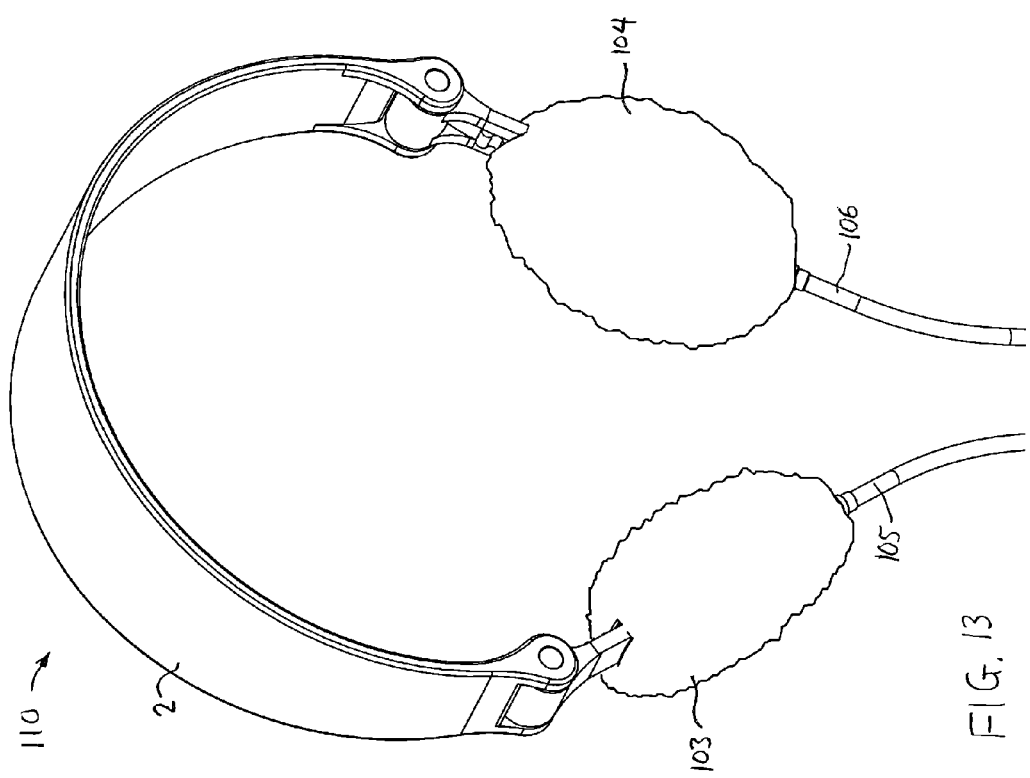
FIG. 13 is a perspective view of a set of headphones with the audio earpieces replaced by audio/earmuff combination earpieces, according to an embodiment of the disclosure.
Figure 14D:
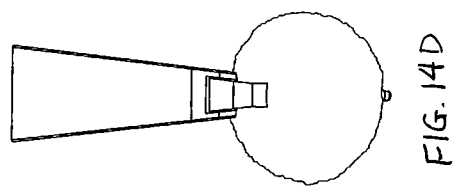
FIGS. 14A-14F are respectively front, left, rear, right, top and bottom views of the headphones of FIG. 13.
Figure 14F:
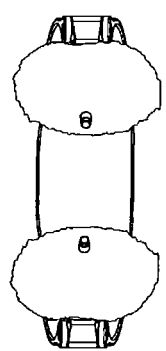
Figure 14C:
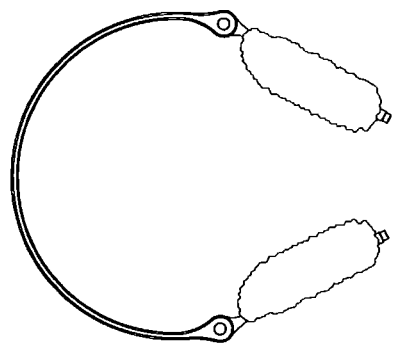
Figure 14E:
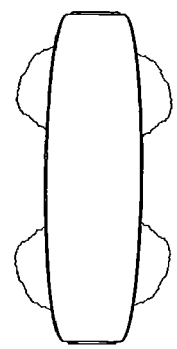
Figure 14B:
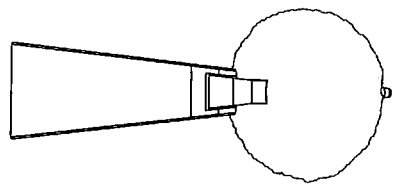
Figure 14A:
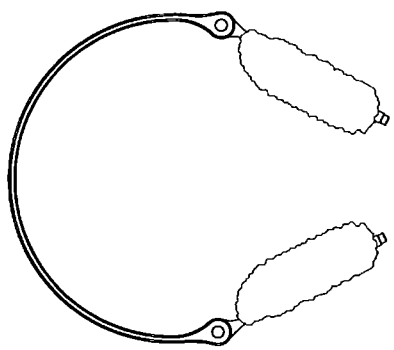

In another embodiment, the audio earpieces are replaced by earmuffs, but the earmuffs also have speakers therein and may be connected to an audio source. FIG. 13 shows an audio/earmuff combination 110 where audio-enabled earmuffs 103, 104, connected by wires 105, 106 to an audio source (not shown), are connected to headband 2. In this embodiment, the outer layer (typically soft and padded) of earmuffs 103, 104 completely covers the speaker, speaker cover and end cap, and has openings only for the adjustment member and the audio connector. FIGS. 14A-14F are respectively front, left, rear, right, top and bottom views of the audio/earmuff combination headphones of FIG. 13.

Figure 15:
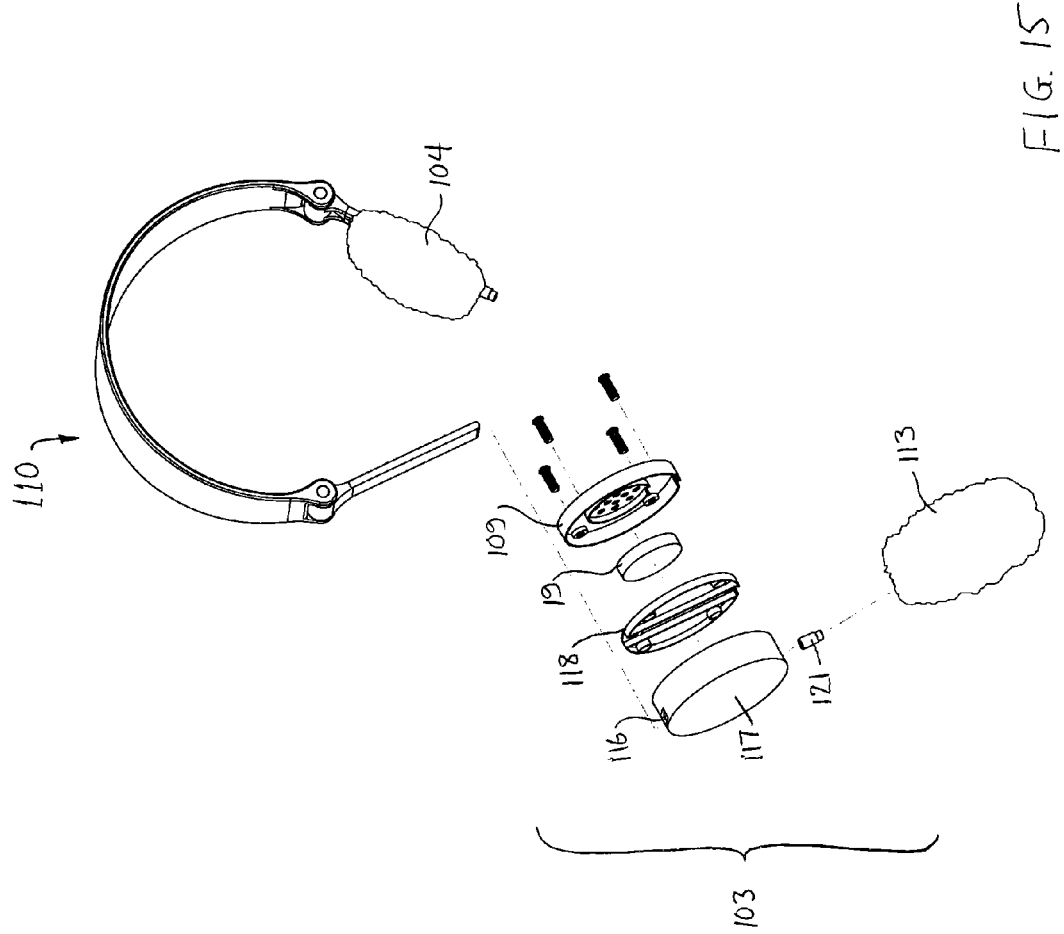
FIG. 15 is a partially exploded view of the headphones of FIG. 13, showing details of an audio/earmuff combination earpiece according to an embodiment of the disclosure.

FIG. 15 is a partially exploded view of audio/earmuff combination headphones 110 according to an embodiment of the disclosure. Speaker 19 fits into a recess at the back side of speaker cover 109. Speaker cover 109 and channel plate 118 are secured to each other and to end cap 117. End cap 117 has a disc shape to provide the desired shape for the earmuff when covered by the outer layer. Channel plate 118 fits into end cap 117 so that a channel formed at the back side of channel plate 118 is aligned with opening 116. Outer layer 113 fits over these other components, completely covering them except for opening 116 and providing access to the audio signal via connector 121.

Replacement of the earpieces is not limited to earmuffs. It will be appreciated that any item for covering an ear, having a channel and tab structure as described above, may be attached to the headband in the same manner as earpieces 3, 4. For example, earpieces with padding in various colors, and/or earmuffs or ear protectors of various colors and designs may be attached as desired. These earpieces may include audio speakers, similar to the audio/earmuff combination earpieces described just above.

While the disclosure has been described in terms of specific embodiments, it is evident in view of the foregoing description that numerous alternatives, modifications and variations will be apparent to those skilled in the art. Accordingly, the disclosure is intended to encompass all such alternatives, modifications and variations which fall within the scope and spirit of the disclosure and the following claims.

We claim:

1. Adjustable and convertible headphones comprising:
   a headband, having an end having headband holes formed therethrough;
   an adjustment member, having an end having adjustment member holes formed therethrough that are coaxial to the headband holes, a hollow formed in the interior thereof surrounding a pin protruding through said headband and adjustment member holes, and a tab radially intruding into the hollow;
   an earpiece, having an opening and a channel formed therein for receiving the adjustment member, the earpiece thereby slidably connected to the adjustment member;
   the adjustment member and the earpiece in combination including a detent mechanism for resisting sliding movement of the earpiece with respect to the adjustment member; and
   the end of the adjustment member being connected to the end of the headband by a hinge, the hinge including a spring mechanism disposed in the hollow and configured so that rotation of the adjustment member with respect to the headband in a first direction causes the tab to contact and compress the spring mechanism, and rotation of the adjustment member with respect to the headband in the second direction does not cause the tab to contact the spring mechanism, whereby the hinge is spring-loaded in a first direction and not spring-loaded in an opposite second direction.

2. The headphones according to claim 1, wherein the spring mechanism is a coil around the pin, and said rotation in the first direction causes the tab to contact an end portion of the coil.

3. Adjustable and convertible headphones comprising:
   a headband;
   an adjustment member having an end connected to an end of the headband by a hinge, and having a plurality of notches formed in a side thereof;
   an earpiece having an opening and a channel formed therein for receiving the adjustment member, said channel having a wall having a slot formed therein partially separating a tab portion of the wall from a main portion of the wall, the tab portion having a protrusion extending toward said side of the adjustment member and sized to fit each one of the notches;
   the tab portion being flexible with respect to the main portion of said wall; whereby flexing said tab portion to unseat the protrusion from a first notch, in response to force applied in a direction along the channel, permits the adjustment member to slide in the channel; and
   the hinge including a spring mechanism so that rotation of the adjustment member with respect to the headband via the hinge is spring-loaded in a first direction and not spring-loaded in an opposite second direction.

4. The headphones according to claim 3, wherein flexing said tab portion to unseat the protrusion from a first notch, in response to force applied in a direction along the channel, permits the adjustment member to slide in the channel, the protrusion subsequently seating in a second notch.

5. The headphones according to claim 3, wherein flexing said tab portion to unseat the protrusion from a first notch, in response to force applied in a direction along the channel, permits the adjustment member to slide out of the channel, the earpiece thereby being disconnected from the headband.

* * * * *